United States Patent [19]

Casenhiser

[11] Patent Number: 4,694,843
[45] Date of Patent: Sep. 22, 1987

[54] FINGERTIP COVER

[76] Inventor: Elaine J. Casenhiser, 379 Lindenwood Ave., Akron, Ohio 44301

[21] Appl. No.: 916,116

[22] Filed: Oct. 7, 1986

[51] Int. Cl.[4] .................. A45D 29/00; D05B 91/04
[52] U.S. Cl. .................................. 132/73; 2/21; 223/101
[58] Field of Search .......... 132/73, 73.5; 128/77; 2/21; 223/101

[56] References Cited

U.S. PATENT DOCUMENTS

| | | | |
|---|---|---|---|
| 478,356 | 7/1892 | Paige | 132/73 |
| 622,386 | 4/1899 | Peery | 2/21 |
| 1,135,382 | 4/1915 | Kindred | 2/21 |
| 1,380,960 | 6/1921 | Hmenia | 2/21 |
| 1,879,609 | 9/1932 | Hannon | 2/21 |
| 2,013,290 | 9/1935 | Rohrbach | 63/2 |
| 2,409,101 | 10/1946 | Brittingham | 2/21 |
| 2,717,799 | 9/1955 | Jones | 2/21 |
| 2,941,535 | 6/1960 | Lappe | 132/73 |
| 3,070,804 | 1/1963 | Parrilla | 2/21 |
| 3,228,033 | 1/1966 | Ames et al. | 2/21 |
| 3,487,831 | 1/1970 | Jaume et al. | 128/132 |
| 3,967,631 | 7/1976 | Kosal | 132/73 |
| 3,972,325 | 8/1976 | Bluestone | 2/21 |
| 4,127,222 | 11/1978 | Adams | 2/21 |
| 4,577,648 | 3/1986 | Dinerstein | 132/73 |

FOREIGN PATENT DOCUMENTS

| | | | |
|---|---|---|---|
| 31147 | 7/1981 | European Pat. off. | 132/73 |
| 375555 | 5/1923 | Fed. Rep. of Germany | 223/101 |

Primary Examiner—Paul J. Hirsch
Attorney, Agent, or Firm—Olaf Nielsen; Frederick K. Lacher

[57] ABSTRACT

A flexible tubular finger-end sheath has a cavity comprised of an open-end finger-gripping portion and a closed-end protector portion separated by a finger-stopping barrier. The walls of the protector portion converge and terminate in a truncated pressing face at the closed end. Additional stiffening may be provided to the protector-portion by a longitudinal rib thereon.

8 Claims, 6 Drawing Figures

FINGERTIP COVER

TECHNICAL FIELD

The invention is broadly directed to a cover which protects a fingertip and fingernail from damage, while providing a finger end which is stable and remains capable of manipulation.

BACKGROUND OF THE INVENTION

Long fingernails, while fashionable, commonly invite breaking, cracking and splitting while the wearer is occupied in business endeavors, unless they are otherwise protected. Protective devices already proposed include, for example, supports adhered to the underside of nails, such as the cushion of Bluestone U.S. Pat. No. 3,972,325 (1976); other means include a detachable nail, such as in Rohrbach U.S. Pat. No. 2,013,290 (1935), wherein a covering member engages the upper surface of the nail and clips around it. Jaume U.S. Pat. No. 3,487,831 (1970), Kindred U.S. Pat. No. 1,135,382 (1915) and Lappe U.S. Pat. No. 2,941,535 (1960) are further examples of nail shields adhered to upper faces of the original nail. Parrilla U.S. Pat. No. 3,070,804 (1963) provides outer and inner support surfaces for a protruding nail. In Kosal U.S. Pat. No. 3,962,631 (1976) is disclosed an expandable, split cap having a window which exposes the ball of the fingertip. Brittingham U.S. Pat. No. 2,409,101 (1946) addresses the problem of enhancing the use of the hand and its nails by providing them with claws; a protective slot may extend forward of the finger pocket, which is molded with special surfaces adapted to cooperate and grip therebetween.

None of the nail covers disclosed in the art, whether they cover and support the top or bottom of a nail, provide a longitudinal tubular chamber, divided into a nail-protecting and a finger-gripping portion, reinforcements for pressing, and an end having a pressing face.

SUMMARY OF THE INVENTION

The present invention has for one of its objects the provision of a fingertip cover which will give improved protection to a fingernail or an injured fingerend, while allowing finger functions to continue. Another object is to provide a striking surface for precise pressing of keys and buttons with a finger having a long fingernail. This is achieved by the provision of a flexible, relatively soft sheath having a cavity portion which encircles and grips the finger, and a protector portion extending from the finger-gripping portion and separated from it by a transverse barrier or stop. The walls of the protector portion may be inclined or shaped to provide improved rigidity therein; the protector portion can be reinforced with a rib extending longitudinally from the barrier forward to the closed end of the protector portion.

To facilitate, for example, the office use of the cover, it may further be provided with a longitudinal groove in its outer surface for ease in holding and maneuvering a pen or pencil. Likewise, the aforementioned closed forward end may have its exterior surface flattened or truncated for easier, more precise, pressing of the keys of a typewriter or a computer with a finger having a long fingernail.

These and other objects of the present invention will become evident from the embodiment hereinafter described and claimed.

DESCRIPTION OF A PREFERRED EMBODIMENT

Reference is now made to a preferred form of the inventive fingertip cover, as shown in FIGS. 1–6 of the drawings.

Figure 1:
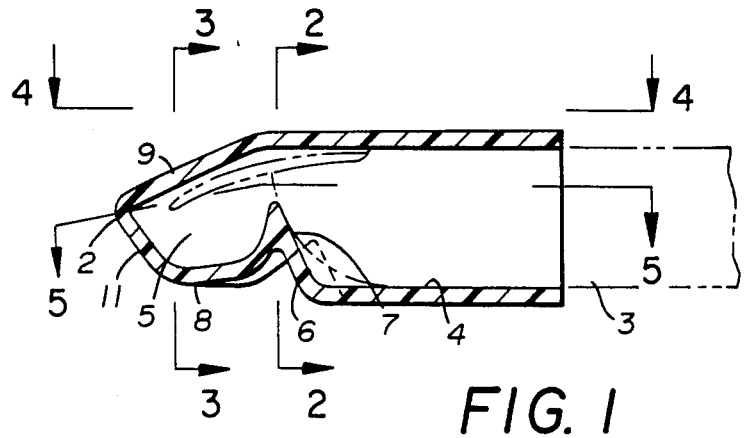
FIG. 1 is a longitudinal, vertical cross-sectional view of the cover of the invention, showing, in phantom, an inserted finger-end with associated nail.
Figure 2:
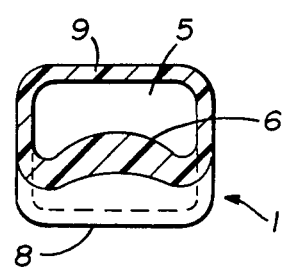
FIG. 2 is a vertical cross-sectional view of the cover, taken generally along line 2—2 of FIG. 1.
Figure 4:
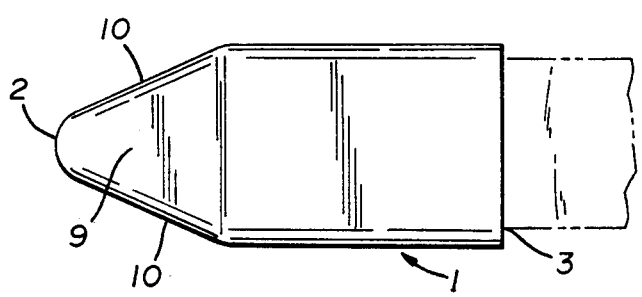
FIG. 4 is a top plan elevation of the cover, taken along line 4—4 of FIG. 1.

As seen most easily from FIGS. 1 and 4, the cover has the basic form of an elongate, continuous tubular sheath 1, closed at its front end 2 and open at the opposite, rear end 3. The resulting cavity is generally divided into a finger-gripping portion 4 and a protector portion 5. The sheath 1 should be of material sufficiently flexible and soft so that its finger-gripping portion 4 may easily slip onto and comfortably encircle the outer joint of a finger, such as that indicated by the phantom lines in FIG. 1. At the same time, the material must be such as to make the protector portion 5 self-supporting as well as useful for performing normal digital skills associated with office work, such as writing and pressing computer and machine keyboards.

A plastic such as, for example, polyvinyl chloride has been found useful for the manufacture of the sheath 1, and is disclosed as an example of the class of materials envisioned.

Specifically, the inventor has found that a wall thickness of approximately 0.04 inches (1.02 mm) produces a sheath 1 well-suited for the above purposes; for certain other applications, wall thicknesses in the range of 0.02 to 0.08 inches (0.51 to 2.03 mm) could be useful.

Extending forwardly from the open rear end 3 of the sheath 1, the finger-gripping portion 4 terminates generally at a stop or barrier 6. The barrier 6 has a wall 7 which extends upwardly from an inside surface of the sheath 1, and runs transversely thereof. The barrier 6 constitutes a stop which limits the extent to which the user's finger may be inserted into the sheath 1. The wall 7 may therefore slope upwardly and forwardly toward the front end 2 of the sheath 1, and may also be curved in the transverse direction to accommodate the contour of the inserted finger.

Figure 3:
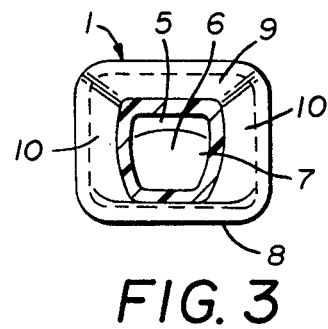
FIG. 3 is a vertical cross-sectional view of the cover, taken generally along line 3—3 of FIG. 1.

Beyond barrier 6, the cavity opens into a protector portion 5, which may be stiffened to provide the desired rigidity. The cross-sectional area of the cavity, as shown in FIGS. 1 and 3, diminishes toward the closed end 2. The exterior wall surfaces of the protector portion 5 are generally parallel to the inner cavity-defining surfaces. Thus a lower wall 8 and an upper wall 9 of the protector portion 5 slope toward the closed end 2. Simultaneously, side walls 10,10 converge forwardly. The four walls 8, 9, and 10,10 join at forward end 2 where a truncated, substantially flat, exterior pressing surface 11 is provided, which is useful for pressing keyboard devices.

In cases where junctions between the four walls 8, 9, and 10,10 of the protector portion 5 are less defined, it will be seen that the walls become substantially conical, and the lower wall 8 thus would be the portion nearest the base of barrier 6.

In the example shown, it will be noted that upper wall 9 slopes more sharply than does lower wall 8, which gives the protector portion 5 a cavity shape generally conforming to the curve of the fingernail it protects.

Figure 6:
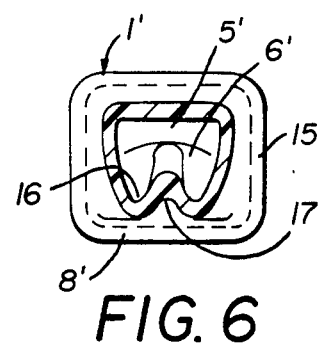
FIG. 6 is a view similar to FIG. 3 but showing modifications to the invention.
Figure 5:
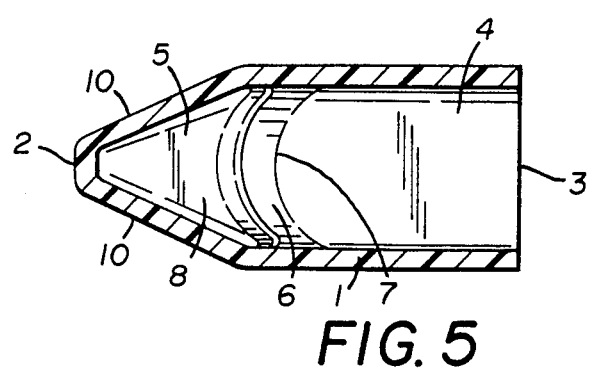
FIG. 5 is a cross-sectional view of the cover, taken generally along line 5—5 of FIG. 1.

In FIG. 6 is shown a first modification, wherein the protector portion 5' is provided with a reinforcing rib 15 rising upwardly from its lower surface 16 and extending generally longitudinally from the barrier 6' forward toward or to the closed end 2'. Such a reinforcing rib 15 provides additional rigidity.

FIG. 6 also shows a second modification, designed to increase the utility of the sheath 1'. A groove 17 is formed in the exterior surface or lower wall 8', and extends forwardly from the area of barrier 6' toward the truncated surface 11. It is envisioned that a writing instrument may be gripped more securely against lateral movement where such a groove 17 tends to match a surface or an edge of a pencil.

Both modifications of rib 15 and groove 17 may, of course, coexist in one sheath 1', giving increased stability and gripping of the protector portion 5'.

It will be seen that the inventor has devised a novel, improved and useful finger-end cover or sheath 1 which will provide increased protection to fingernails against injury, breakage, cracking and splitting. The sheath 1 will also, through the unique shape of the interior stop barrier 6, provide the theraputic benefit of protecting a finger-end which has been accidentally cut or injured, or has undergone surgery.

To meet these requirements, the sheath 1 is made of a soft, flexible material which will conform to a finger shape at the finger-gripping portion 4 and will provide the desired rigidity and stability at the protector portion 5 enhanced by converging walls 8, 9, 10,10, a truncated surface 11, and the interior rib 15. Tightness of fit, choice of material and thickness thereof, as well as longitudinal dimensions will thus coact to provide strength, comfort, and usefulness for digital purposes.

Though the foregoing represents a preferred embodiment, it will be understood that further modifications may occur to those skilled in the art, without thereby limiting the scope of this invention.

What is claimed is:

1. A finger-end cover comprising an elongate, flexible sheath having a closed front end and an open rear end, with a continuous tubular cavity extending therebetween, a stop barrier dividing said cavity into a front protector portion and a rear finger-gripping portion, said protector portion including stiffening means to resist collapse of the walls of said sheath, said gripping portion adapted to receive and retain a finger-end inserted therein no further than to said barrier, at which finger end location the said protector portion is adapted to surround and protect a nail on the finger end.

2. A finger-end cover as in claim 1 wherein said stiffening means comprises diminishing the transverse cross section of said protector portion toward said closed front end.

3. A finger-end cover as in claim 1 wherein said stiffening means comprises converging of the walls of said protector portion toward said front end.

4. A finger-end cover as in claim 1 wherein the wall of said stop barrier slopes upwardly and forwardly within said sheath cavity, and curves transversely thereof.

5. A finger-end cover as in claim 1 wherein said stiffening means includes a reinforcing rib extending longitudinally along the inner wall of said protector portion between said stop barrier and said closed end.

6. A finger-end cover as in claim 1 including a flattened exterior pressing surface on the said closed end of said protector portion.

7. A finger-end as in claim 1 including a longitudinal groove in the outer surface of said protector portion between the area of said stop barrier and the said closed end.

8. A finger-end cover comprising an elongate, flexible plastic sheath having a closed front end and an open rear end, with a continuous tubular cavity extending therebetween, a barrier dividing said sheath cavity into a front protector portion and a rear finger-gripping portion, the wall of said barrier sloping upwardly and forwardly in said cavity and curving transversely thereof, the walls of said sheath in said protector portion converging toward said closed front end and terminating in a truncated substantially flat pressing surface, a reinforcing rib located interiorly of said protector portion and a groove located exteriorly of said protector portion, said rib and said groove extending longitudinally between the area of said barrier and said closed front end, said gripping portion adapted to receive and retain a finger end and associated nail, with the finger end stopped at said barrier, and the nail extending freely beyond said barrier and into the said protector portion.

* * * * *